United States Patent
Hartzell et al.

[11] Patent Number: 5,230,207
[45] Date of Patent: Jul. 27, 1993

[54] EQUIPMENT FOR MANUFACTURING OF SUBCUTANEOUS CAPSULES

[76] Inventors: Rolf Hartzell, Loukkaantie 16, SF-20300 Turku; Timo Helle, Talinkorventie 9 A, SF-20310 Turku; Pekka Lankinen, Pyynkatu 12, SF-20600 Turku; Pekka Nieminen, Hanhijoentie 18, SF-21540 Preitilä, all of Finland

[21] Appl. No.: 721,457
[22] PCT Filed: Mar. 28, 1991
[86] PCT No.: PCT/FI91/00090
§ 371 Date: Jul. 3, 1991
§ 102(e) Date: Jul. 3, 1991
[87] PCT Pub. No.: WO92/17148
PCT Pub. Date: Oct. 15, 1992
[51] Int. Cl.$^5$ .................. B65B 1/02; B65B 1/12; A61J 3/07
[52] U.S. Cl. .................. 53/547; 53/560; 53/567; 53/900
[58] Field of Search .............. 53/560, 547, 567, 900, 53/454, 459, 471

[56] References Cited
U.S. PATENT DOCUMENTS

| | | | |
|---|---|---|---|
| 3,353,328 | 11/1967 | Wheeler et al. | 53/547 X |
| 4,028,024 | 6/1977 | Moreland | 53/900 |
| 4,247,006 | 1/1981 | Bodenmann et al. | |
| 4,307,555 | 12/1981 | Mlodozeniec et al. | 53/560 X |
| 4,884,602 | 12/1989 | Yamamoto et al. | 53/560 X |
| 4,964,262 | 10/1990 | Moser et al. | 53/900 X |

FOREIGN PATENT DOCUMENTS 2390947 12/1978 France.
2213455A 8/1989 United Kingdom.

Primary Examiner—Horace M. Culver
Attorney, Agent, or Firm—Wolf, Greenfield & Sacks, P.C.

[57] ABSTRACT

The invention relates to an equipment for manufacturing subcutaneous capsules. The capsules are produced by cutting from a silicone tube lengths in excess of the final capsule length. The lengths are arranged into rows including a defined number of them and in these rows they are filled and sealed. One end of the capsules is first sealed by glue dosaged into their openings. The material for the capsules is dosaged by an aperture disc glidable on a plane surface. By sweeping the upper surface of the disc the dosage volume is limited to the volume defined by the aperture. To regulate the packaging density of the material vibration may be used during the filling of the apertures. The dosaged material is conveyed to the capsule via a feeder funnel, through which a rotatable spiral spring, functioning as a filling screw, is inserted into the capsule to be filled.

4 Claims, 7 Drawing Sheets

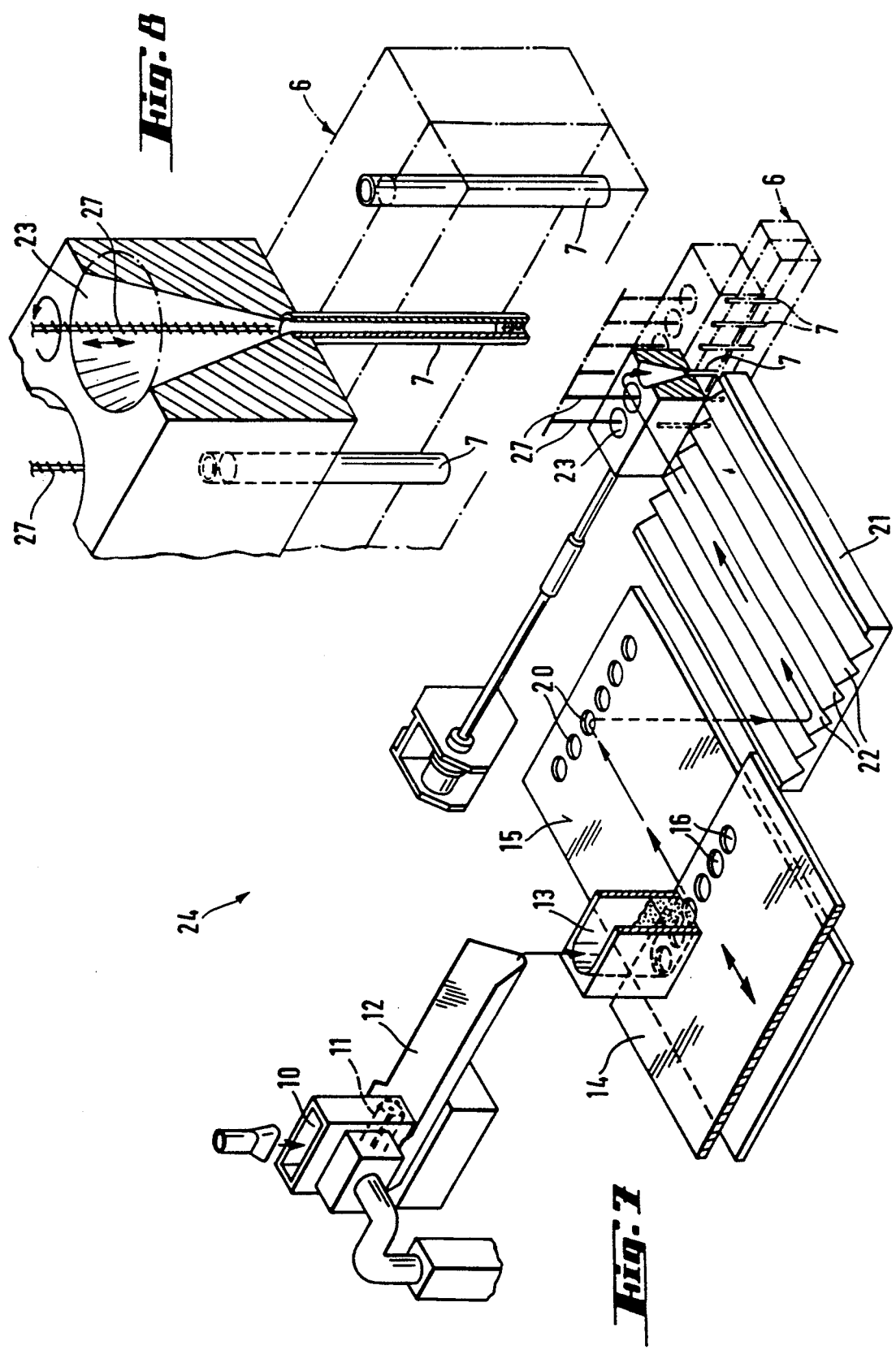

EQUIPMENT FOR MANUFACTURING OF SUBCUTANEOUS CAPSULES

The present invention relates to an equipment for manufacturing of capsules filled with a medical substance essentially in powder form, which capsules are intended to be implanted under the skin and from which the medical substance will diffuse into the blood circulation through the wall material of the capsules. Intended uses are i.a. dosage of hormones, especially contraceptive hormones as well as of antabus agents.

A problem in the dosage of contraceptive hormones has been above all the small amount of hormone substance to be portioned accurately in powder form dosages into the smallsized capsules. The amount of substance diffusing from the capsule is proportional to the amount of substance in the capsule and therefore, to assure a correct and in all cases a truly predictable liberation, the capsules should include exactly the same amount of substance. In the said hormonal use, the tolerances allowed are ±5%, which accuracy is extremely difficult to reach with the prior used manual dosing. The manual dosing method is, naturally, also a very expensive stage in the production of the capsules because of the great need of human workforce.

The invention relates to providing a totally automatic manufacturing process for subcutaneous capsules filled with a medical substance, whereby the uniformity of the end result is essentially better than that of corresponding prior art processes, involving partly manual stages.

In capsule production the starting point is a tube for forming the casing of the capsule, and for which a suitable material is a silicone plastic. The diameter of the tube for manufacturing of hormone capsules is 1.5 mm. The tube is fed to the capsule manufacturing line as continuous lengths from a suitable apparatus. At the starting point of the capsule manufacturing line, the tube is cut into capsule blanks of a suitable length, e.g. to lengths of about 34 mm.

The said blanks are then arranged into a row formed by several blanks. One row may comprise e.g. 12 blanks. The position of the blanks is advantageously chosen in conformity with the handling positions of the tube in the preceeding cutting device. One of such rows is advantageously joined together and it will then form a handling unit for the next process stages. In order to assemble this handling unit row it is possible to use a means to keep the blanks in their prescribed positions and with the help of which the handling unit row is transferred from one stage to another in the process, as well as positioned for each process stage. The said means can advantageously be a cassette of a clamping claw structure where the claws are in a mutual spring loaded clamping contact and where mutually co-operating indentation slots have been formed on the contact faces of the claws in order to form through holes for receiving the capsule blanks. The claws are made to retract from each other against the said spring load to receive the capsule blanks. The operation of the said cassette is advantageously synchronized with the capsule blank cutting device.

To make the capsule blank fillable, one of its ends has to be sealed. In the apparatus according to the application, this stage is carried out so that one end of the tubes forming the capsule blanks receives a small amount of glue, e.g. a silicone glue, that adheres well to the tube material forming the capsule wall. The glueing is carried out by using a very thin nozzle needle inserted to a depth of about 1.6 mm in the capsule blank. The glue is discharged from the nozzle simultaneuously when the nozzle needle is rotated and extracted. By adjusting the speed by which the nozzle needle is extracted it is possible to regulate the amount of glue remaining in the capsule blank. This possibility is utilized in the process according to the application to eliminate the impacts of the viscosity fluctuations of the glue, by monitoring the load on the glue pump and regulating the speed by which the nozzle needle is extracted in relation to the load. A high viscosity glue, discharged slowly from the needle, will load the dosing pump more than a low viscosity glue. Whenever the load on the dosing pump is rising, the speed by which the needle is extracted is slowed down.

The glue fed to the end of the capsule blank is hardened by a suitable accelerator, e.g. using humidity or heating. After the hardening of the glue there is the possibility, whenever desired, to use a finishing treatment of the sealed end by cutting out a part of the end of the capsule blank, from the area sealed by glueing. After sealing the capsule blanks, the blank row is turned so that the ends still left open are facing upwards. In this position the capsule blanks are forwarded to the filling stage.

The filling stage involves as an essential element the dosing of the mass of material to be fed into the capsule blank. In the process according to the application, a device is used in which the dosing is based on a disc glidable along a plane surface and having through apertures determining the dose quantities. The material to be dosed is fed to the apertures closed by the lower plane surface, and the correct quantity is finalized by sweeping any extra material away at the respective apertures to the upper surface level of the disc. The quantities thus dosed are delivered, individually to each capsule blank, by moving the disc along the plane surface to such a position where the lower surfaces of the apertures will be freed.

In the process according to the application the dosed quantity of material are dropped from each aperture to its respective transportation groove made in the surface of a disc, operating as a vibrating conveyor. When the apertures are emptied the dosing disc is transferred back to its filling position. The dosed material quantities proceed in the grooves of the vibrating conveyor further to feeding funnels under which the capsule blanks, carried by the clamping claw cassette, have been conveyed. In order to promote the flow of the material quantities into the capsule blanks, a special spiral feeder is used. The said feeder comprises a spiral spring that has a diameter less than the inner diameter of the capsule blank, and a straight steering wire therein. This spring is rotatable in the forward direction of its spiral.

As far as the feeding process itself is concerned, the procedure is carried out so that the spiral spring is inserted into the capsule blank and made to rotate. Simultaneously with the activation of the rotative movement the raising of the spiral spring from the capsule blank is initiated. When the rotation direction is as said above, the spring acts as a feeder screw. When the filling of the capsule blank advances, the spiral spring is extracted, still in rotation, from the capsule blank. During the said operational stages the feeding funnels are kept under vibration. When the head of the spiral spring has risen to the desired material filling level its rising movement is stopped, but vibration, and rotation of the spring are continued. Thus, the spiral spring determines the height of the material column fed to the capsule.

After the filling stage, it is advisable to clean the inner surfaces of the open ends of the capsule blanks to remove any adhered filling material to ensure the sealing of the ends of the capsule blanks without problems. The cleaning may be carried out on the inside of the mouth area of the capsule blank by using a scraping rotating mandrel or a corresponding brush. The ends of the capsule blanks are sealed by using similar procedures as in connection with the above described closing of the first ends of the capsule blanks. After the glue used in the sealing process has hardened, the capsule ends may be similarly finished by cutting parts away from their sealed portions.

After these stages the completed capsules are conveyed through as such known process stages, whereby the capsules are washed, dried, inspected, packaged and sterilized to ready-to-use products.

In the following, the invention will be described referring to the annexed drawing where:

FIG. 7 shows a simplified flow chart according to FIG. 6, and

FIG. 8 shows a magnified detail from the area of the feeding funnels.

Figure 1:
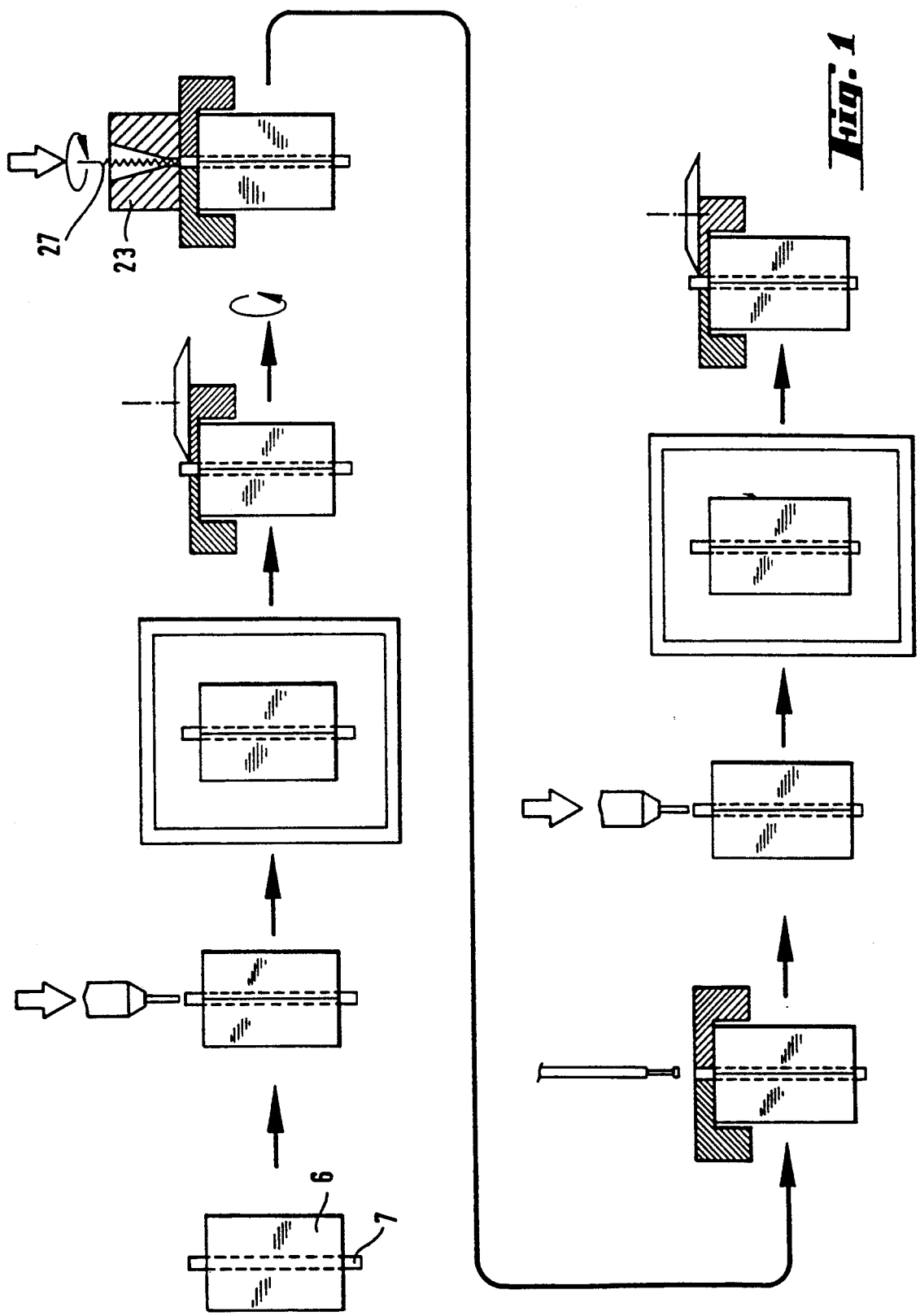
FIG. 1 shows a flow chart of the process according to the application in principle.

In the basic flow chart according to FIG. 1 the process stages are shown in the advancing order principally as described above.

Figure 2:
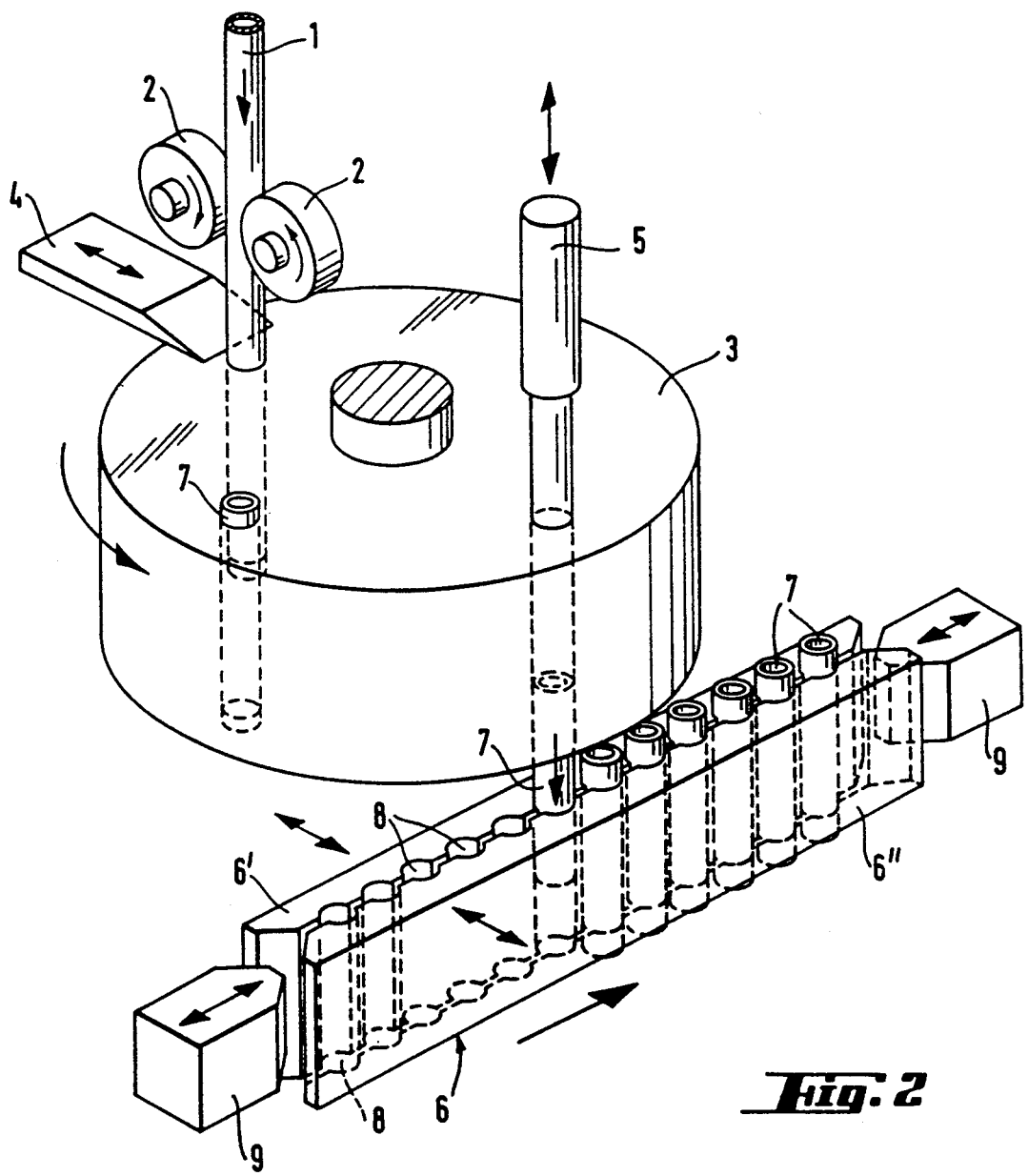
FIG. 2 shows an embodiment of an apparatus in principle, for cutting the capsule blanks and their arrangement in handling unit rows.

The first stage of the process, i.e. the cutting of the capsule blanks and their arrangement to rows forming the handling unit, is described in more detail in the drawing FIG. 2.

The silicone tube 1 forming the casing of the capsule blanks is fed as a continuous length from a coil, guided by two feeder rolls 2, to an aperture made in a disc 3 rotatable around a vertical axle. The aperture is a through hole and its diameter is designed to match the outer diameter of the tube so that the cut tube stays in the aperture without any separate supporting means, partly due to the distortion tendency caused by the material memory of the tube. In connection with the tube feeding station there is a cutter device 4 by which the tube is cut to the upper surface level of the disc. The length of the capsule blank to be cut may be determined by the duration of the rotation movement of the feeder discs 2.

By rotating the disc around its vertical axle, it is possible to move the capsule blank, formed by the cut tube, to a discharge station where the capsule blank is taken from its aperture by a punch-through mandrel 5. From the point-of-view of the flexible operation of the apparatus, it is advantageous to have several through apertures in the disc 3 whereby the cutting of a new blank and the discharging of the previous blank may be carried out as simultaneous operations.

The operation of the cutting device is advantageously synchronized with the device arranging the cut capsule blanks. As such a device arranging the capsule blanks it is advantageous to use a spring-loaded clamping claw cassette 6 consisting of two opposite co-operating halves 6' and 6". The halves are separated from each other by a vertical dividing plane, the separating surfaces being furnished with essentially semi-circular opposite grooves traversing the dividing plane, that, when operating together, form the through apertures 8 receiving the capsule blanks 7. The apertures 8 have been placed at an even distance from each other, and the clamping claw cassette 6 has been arranged to be moved stepwise with steps of respective length in the direction of the row of apertures to receive the capsule blanks 7 coming from the cutting device.

To facilitate the reception of individual capsule blanks 7 from the cutting device, the clamping claw cassette 6 has been arranged to be opened, to a limited extent, for each receiving operation. This opening capability has been provided by two wedges 9, acting in the division plane at the ends of the cassette, which wedges can be pushed towards each other in the division plane.

By means of these wedges, the clamping claw cassette 6 halves, may be retracted from each other against the springloaded (not shown) force pressing them against each other. The springload may be provided for, e.g. in connection with screw joints joining the clamping claw cassette halves, by spring washers or similar devices, as the opening movement does not need to be very big in relation to the diameter of the capsule blank.

Deviating from the embodiment shown in the drawing FIGS. 1 and 2, the disc 3 of the cutting device may also be arranged to rotate around a horizontal axle and, respectively, the clamping claw cassette 6 arranged to receive the cut capsule blanks in horizontal positions.

The capsule blanks are conveyed, carried by the said clamping claw cassette 6, to the next processing stages and through them, of which a general description concerning the sealing of the second ends and their trimming has been given above. These operations may be carried out when the capsule blanks are either in a vertical position, as shown in FIG. 1, or alternatively, in a horizontal position. An alternative trimming of the ends may also be combined with the trimming following the sealing of the filling end, to be described later, to a single stage only.

As an important partial stage in the process, the dosing of the material to be packaged into the capsules is described, as well as the equipment relating thereto, referring to the drawing FIGS. 3 to 8. The said equipment is used to dosage the material for each capsule blank and to direct it to the respective capsule along its own path.

The dosing equipment is based on the so-called aperture disc technology, whereby the material mass is dosed by the means of a plate of even thickness movable on a plane surface and provided with through apertures defining the dosage quantities. When the dosage quantities are metered, the disc rests on the said plane surface and the plane surface closes the bottom part of the apertures. The material to be dosed is made to flow into the apertures and the exact quantity is determined by sweeping the excessively fed heap of material away, to the upper surface level of the disc. Then the disc is moved along the said plane surface to a discharging station, where the lower surface of the apertures is opened to a receptacle for the material.

Figure 3:
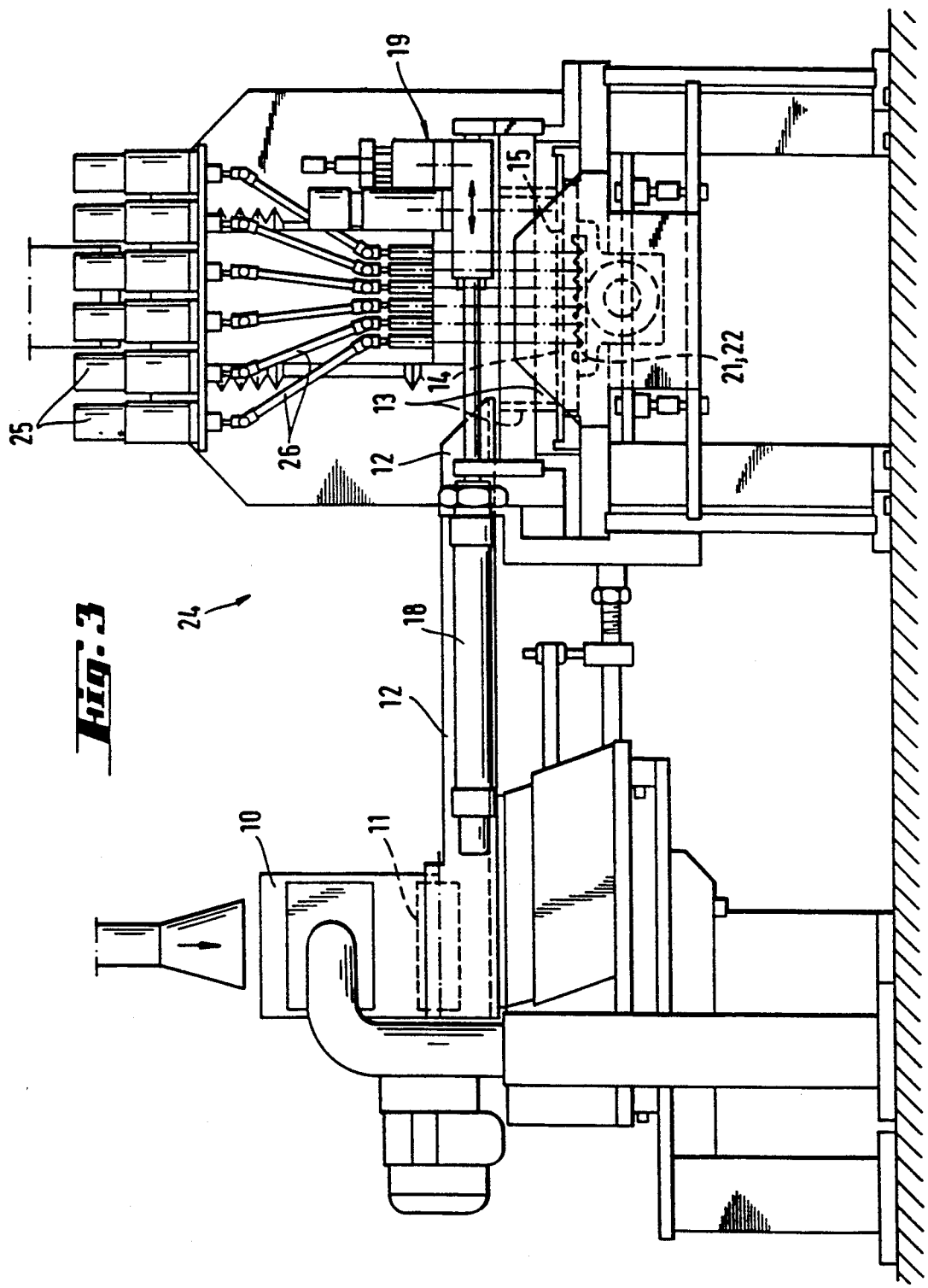
FIG. 3 shows a dosing and filling apparatus seen in the forward direction of the process.

In the device according to FIG. 3, the material used for filling the dosage apertures is fed from a storage container 10 by means of a compartment feeder 11, performing a rough dosing, to a trough-like vibrating conveyor 12. This vibrating conveyor transfers the material to be dosed further to a distribution through 13 at a lower level, the open lower part of which is defined by the dosing disc 14. The dosing disc 14 is glidable on the plane surface 15. The number of through apertures in the dosing disc 14 in the described embodiment is half of that of the capsule blanks to be filled in the clamping claw cassette 6. The parts of the device may naturally also be dimensioned so that the number of the apertures and the number of the capsule blanks to be filled are the same. The diameter of the apertures 16 is dimensioned so, taking the thickness of the aperture disc 14 into account, that the apertures, when filled up to the upper surface level of the disc, will define the volume of the dose intended for each capsule, or so that a dosage volume is formed by a multiple of aperture fillings.

Figure 4:
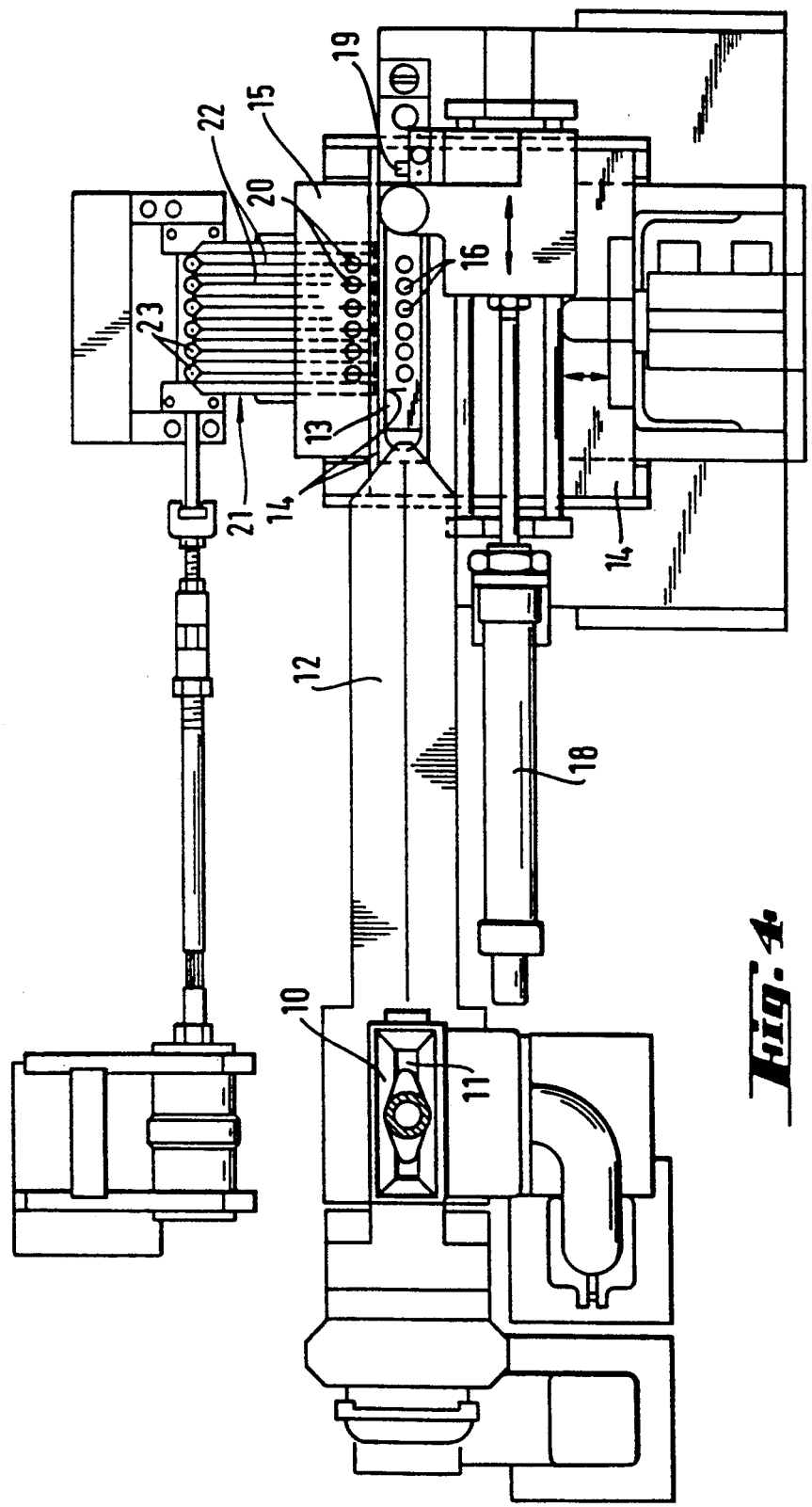
FIG. 4 shows a dosing and filling apparatus seen from above.
Figure 5:
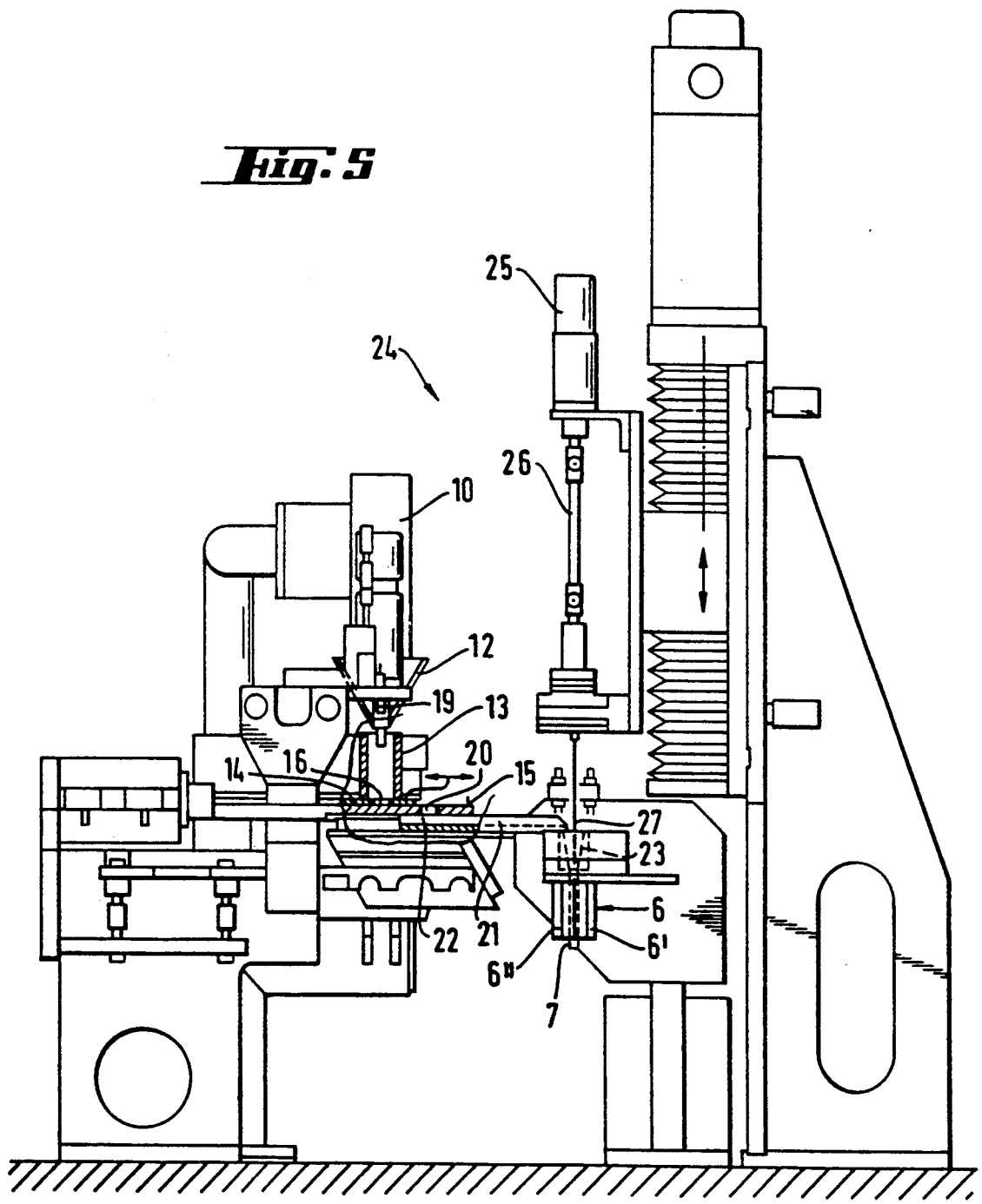
FIG. 5 shows a dosing and filling apparatus seen from the side with respect to the forward direction of the process.
Figure 6:
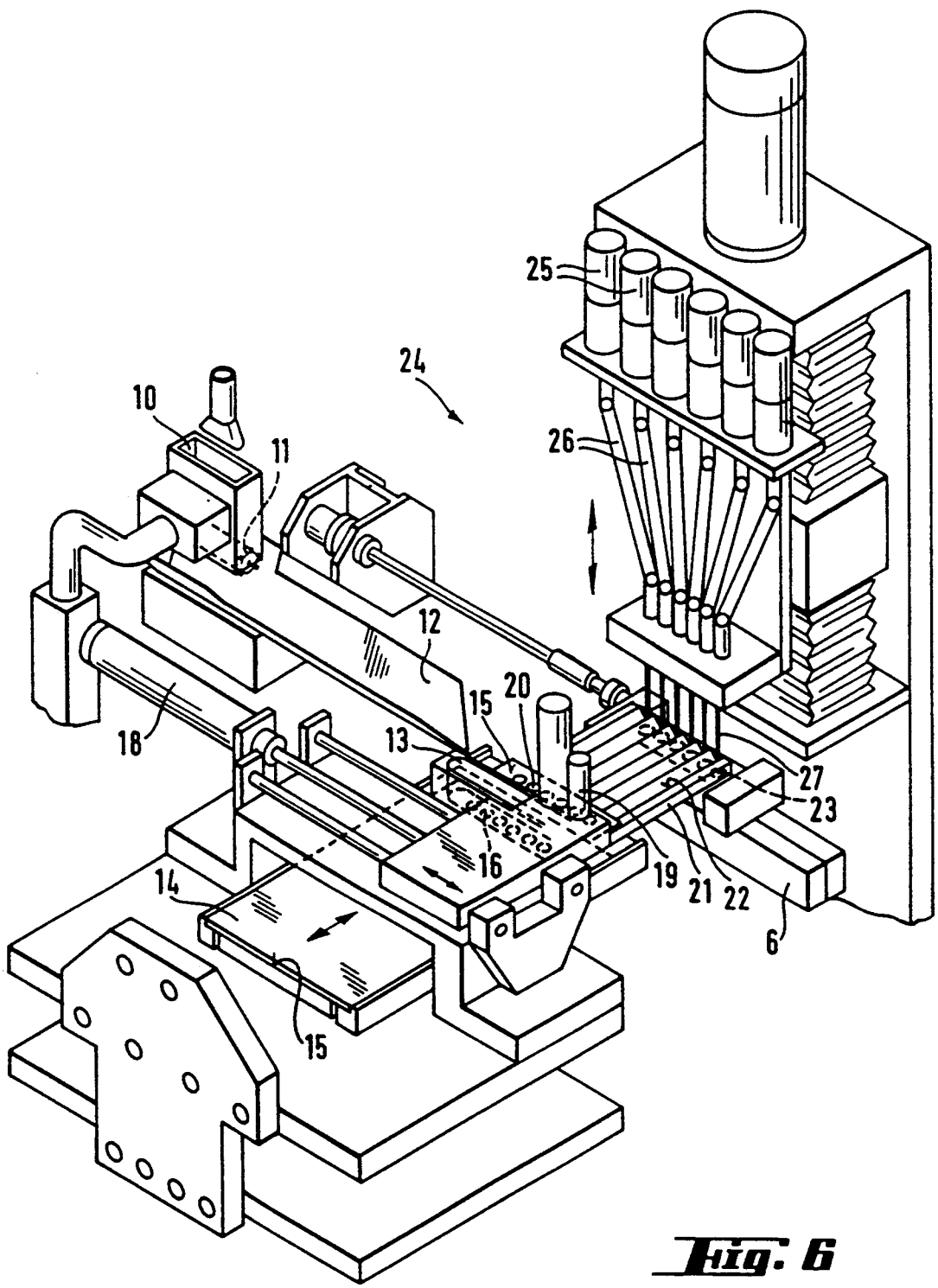
FIG. 6 shows a dosing and filling apparatus axonometrically.

In the device described in the drawing FIGS. 3, 4, and 5 the material to be dosed and transported by the vibrating conveyor 12 is spread in the distribution through 13 by means of a device movable by a cylinder-piston device 18. An optical control device 19 is arranged in connection with the through by means of which the surface level in the distribution through 13 of the material to be dosed is monitored, and on the basis of the information of which the number of the operation cycles of the compartment feeder 11, which functions as a rough dosing device, is determined.

The plane surface 15, on which the dosing aperture disc 14 is glidable and upon which it rests during filling of the dosing apertures, is combined with a suitable vibrating device in order to direct a vibrating effect on the plane surface during the filling stage of the apertures 16. This vibrating effect will act on the packaging density of the material to be filled into the dosing apertures 16. It is possible to regulate the packaging degree by regulating the duration and/or the intensity of the vibration. Another factor influencing the packaging degree is the filling level in the distribution through 13 of the material to be filled monitored by the said optical control device 19.

After filling of the apertures, the dosing disc 14 is pushed along the plane surface 15 to the discharge station of the apertures. The upper surface of the dosing disc 14 is in gliding contact with the lower surface of the distribution through 13 whereby the lower edge of the through levels the dose volumes in the apertures to the upper surface level of the dosing disc 14, whereby the excess material remains in the distribution through 13 closed by the dosing disc 14.

In the level surface 15 there is formed a row of discharge apertures 20 corresponding to the dosing apertures 16, above which row the apertures 16 are glided. Arranged below the discharging apertures 20, there is a vibrating conveyor formed by a groove disc 21. In the groove disc 21 there is the same number of grooves 22 as there are discharging apertures 20, and the grooves and the discharging apertures are aligned so that the material in the dosing apertures can be discharged through the discharging apertures 20 to their respective groove 22 in the groove disc 21. The groove disc 21 is preferably declining and equipped with a vibration device, whereby a groove 22 forms a conveyor for a single dosage.

The dosaged material is transferred on the groove disc 21 to filling funnels 23 arranged in a transverse row beneath the fail edge of the groove disc 21. Below these filling funnels there has in turn been transferred a row of capsule blanks 7 carried by the clamping claw cassette 6, the lower ends of the capsule blanks having been sealed and advantageously trimmed according to the measures described above.

The equipment according to the FIGS. 3 to 8 also comprises a filling apparatus 24, comprising a number of feeding devices corresponding to the number of filling funnels 23. Each feeding device comprises a rotating motor 25, a spindle 26, and a feeder screw 27 attached to the the lower end of the spindle. To operate the feeder screw 27 within the conditions determined by the small dimensions of the capsules to be filled, the filling screw is formed by a thin spiral spring. For better control of the movements of the spiral spring, a thin straight guiding wire is placed inside the spring, extending substantially along the whole length of the spiral spring.

The feeder screw 27 formed by the spiral spring is directed through each feeding funnel 23 to the capsule blank below it and is made to rotate. The rotative movement is naturally chosen in the feeding direction of the spiral spring. The feeder screw rotating in the capsule blank feeds the material fed into the feeder funnel efficiently into the capsule blank. In order to avoid unnecessary compacting of the material in the capsule blank, the feeder screw is raised as filling is advancing. After the dosed batch has been completely fed, the feeder screw is removed completely from the capsule blank, and the blanks are transferred to be sealed. Before sealing, it is possible to clean the inside of their mouth areas to remove any remaining filling material. Sealing is carried out by glueing in the same way as the sealing of the opposite end of the blank before the filling stage.

After sealing, the ends of the filled capsules can be trimmed by cutting. After trimming, the final capsules will be removed from their respective clamping claw cassettes after which operation they will be processed individually according to prior technology discussed briefly above.

We claim:

1. Equipment for manufacturing a subcutaneous capsule filled with a medical substance, from a tube forming the capsule casing, comprising a cutting device for cutting the capsule blanks into fixed lengths, a means for arranging the capsule blanks cut the tube in a parallel fashion in rows including a specific number of capsule blanks, the said arranging means including a clamping claw cassette means for holding the capsule blanks in the said row through the processing stages following the arranging stage, devices for dosing glue to one end of the capsule blanks, devices for hardening the glue, means for turning the cassette means so that the capsule blanks carried thereby turn to a position with their open ends facing upwards, a dosing device, based on a dosing aperture disc glidable along a plane surface, for dosing the medical substance in individual quantities for each capsule, devices for feeding the individually dosed medicine quantities for a respective capsule blank to a feeder, a feeder included for each capsule blank, a rotatable spiral spring means to be inserted into the capsule blank and extracted therefrom, devices for dosing glue into the open ends of the capsule blanks, and means for hardening the glue.

2. Equipment according to the claim 1, wherein the devices for dosing the glue to the ends of the capsule blanks to be sealed comprise a glue nozzle insertable into and extractable from a capsule blank, respectively, the rate of extraction of which can be regulated in order to regulate the amount of glue remaining in the capsule blank.

3. Equipment according to the claim 2, wherein the extraction rate of the glue nozzle from a capsule blank is made directly dependent on the load current of a pump motor feeding glue.

4. Equipment according to the claim 1 comprising means for cutting the ends of the sealed capsules within the area sealed by the glue.

* * * * *